United States Patent
Dekker et al.

(10) Patent No.: US 8,708,922 B2
(45) Date of Patent: Apr. 29, 2014

(54) ELECTRICALLY ISOLATED CATHETER WITH WIRELESS SENSORS

(75) Inventors: Ronald Dekker, Valkenswaard (NL); Antoon Marie Henrie Tombeur, Lommel (BE); Theodorus Martinus Michielsen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1347 days.

(21) Appl. No.: 12/519,817

(22) PCT Filed: Dec. 19, 2007

(86) PCT No.: PCT/IB2007/055216
§ 371 (c)(1),
(2), (4) Date: Jun. 18, 2009

(87) PCT Pub. No.: WO2008/075295
PCT Pub. Date: Jun. 26, 2008

(65) Prior Publication Data
US 2010/0042010 A1    Feb. 18, 2010

Related U.S. Application Data

(60) Provisional application No. 60/871,236, filed on Dec. 21, 2006.

(51) Int. Cl.
*A61B 5/04*    (2006.01)
(52) U.S. Cl.
USPC ............... 600/508; 600/374; 128/903
(58) Field of Classification Search
USPC .............. 607/33, 61; 600/325, 327, 339, 341, 600/377, 508
See application file for complete search history.

(56) References Cited

U.S. PATENT DOCUMENTS

| | | | | |
|---|---|---|---|---|
| 5,016,631 A | * | 5/1991 | Hogrefe | 607/2 |
| 5,833,603 A | * | 11/1998 | Kovacs et al. | 600/317 |
| 6,164,284 A | * | 12/2000 | Schulman et al. | 128/899 |
| 2002/0133201 A1 | * | 9/2002 | Connelly et al. | 607/9 |
| 2003/0078003 A1 | | 4/2003 | Hunter et al. | |
| 2003/0136417 A1 | | 7/2003 | Fonseca et al. | |
| 2005/0027330 A1 | | 2/2005 | Govari | |
| 2006/0116554 A1 | | 6/2006 | Dijkman | |

FOREIGN PATENT DOCUMENTS

| | | |
|---|---|---|
| DE | 4341903 A1 | 6/1995 |
| WO | 2004026120 A1 | 4/2004 |
| WO | 2005120336 A1 | 12/2005 |
| WO | 2006048664 A2 | 5/2006 |
| WO | 2006117154 A1 | 11/2006 |

OTHER PUBLICATIONS

Classbrummel: "Transfer of Automotive Microsystems Into Medical Applications"; Proceedings of the Micro.Tec 2000 VDE World Microtechnologies Congress, Hanover, Germany, September 2000, vol. 2, pp. 315-318.

* cited by examiner

*Primary Examiner* — Mark W Bockelman

(57) ABSTRACT

A local power-delivery/data-reception unit is installed within an insertion end of a sealed catheter. The local power-delivery/data-reception unit wirelessly powers a separately sealed sensor that is attached to the insertion end and configured for wirelessly sending a data signal to the local power-delivery/data-reception unit. The catheter may further feature a remote power-delivery/data-reception unit disposed within the handle and configured for wirelessly communicating with the local power-delivery/data-reception unit and a controller for controlling the sensor.

22 Claims, 6 Drawing Sheets

ELECTRICALLY ISOLATED CATHETER WITH WIRELESS SENSORS

The present application relates generally to catheters using wireless communication and, more particularly, to a new and useful catheter for conducting, within the patient's body, wireless communication with a sensor.

Cardiac catheterization is a common diagnostic test performed to evaluate the condition of the heart muscle, valves and vessels. During the procedure, the physician inserts long, flexible tubes called angiography catheters into the heart and coronary arteries.

A special form of cardiac catheterization is cardiac mapping, which is used with patients having certain types of heart rhythm disorders, caused by small areas of abnormal heart tissue interrupting the heart's normal electrical system. A flexible tube with wires called an electrode catheter is inserted into the heart, by introducing the tube intravenously and manually feeding the catheter into the heart. An array of electrodes at the tip of the insertion end of the catheter can be distributed, to thereby track the heart's electrical signals, affording three-dimensional reconstruction of the heart's electrical functioning.

The mapping electrodes in the array may easily number twenty or more. They are all connected to a connector in the handle by very thin and flexible wires, the length of which is surrounded by a tube or sheath that meets the handle.

Conventional catheters are open and cannot be sterilized. Thus, conventional catheters are expensive disposable devices.

Conventional catheters are also complicated devices to fabricate, due to the connection of many tiny wires through the sheath.

It is desirable to remedy the drawbacks of conventional catheters.

The following specification discloses a novel catheter having a sealed catheter body which includes a handle and an insertion end for insertion into a patient. The catheter further includes a sealed sensor adjoined to the insertion end and capable of sending data signals. The sensor and the catheter body are sealed from each other. A local power-delivery/data-reception (PDDR) unit is incorporated at the insertion end of the catheter body for wirelessly emitting a signal that powers the sensor and for receiving data signals from the sensor.

A method for assembling the novel catheter is also disclosed. The method includes providing a catheter body that has a handle and an insertion end for inserting into a patient. A local power-delivery/data-reception (PDDR) unit to be incorporated at the insertion end of the catheter body is configured for wirelessly emitting a signal that powers a sensor to be adjoined to the insertion end and for wirelessly receiving a data signal from the sensor. The sensor to be adjoined to the insertion end is configured for wirelessly receiving the emitted signal for power and wirelessly sending, to the local PDDR unit, a data signal. The sensor and the catheter body are sealed, separately from each other, and the sealed sensor is adjoined to the insertion end.

The novel catheter is simpler to fabricate, and may be sterilized and re-used.

In addition, the close proximity between the sensor and the local PDDR unit affords efficient transmission of energy in powering the sensor.

These and other aspects will be apparent from and elucidated with reference to the embodiments described hereinafter.

Details of the novel catheter are set forth below with the aid of the following drawings, wherein the same or similar features in different drawings are annotated with the analogous reference numerals:

Figure 1:
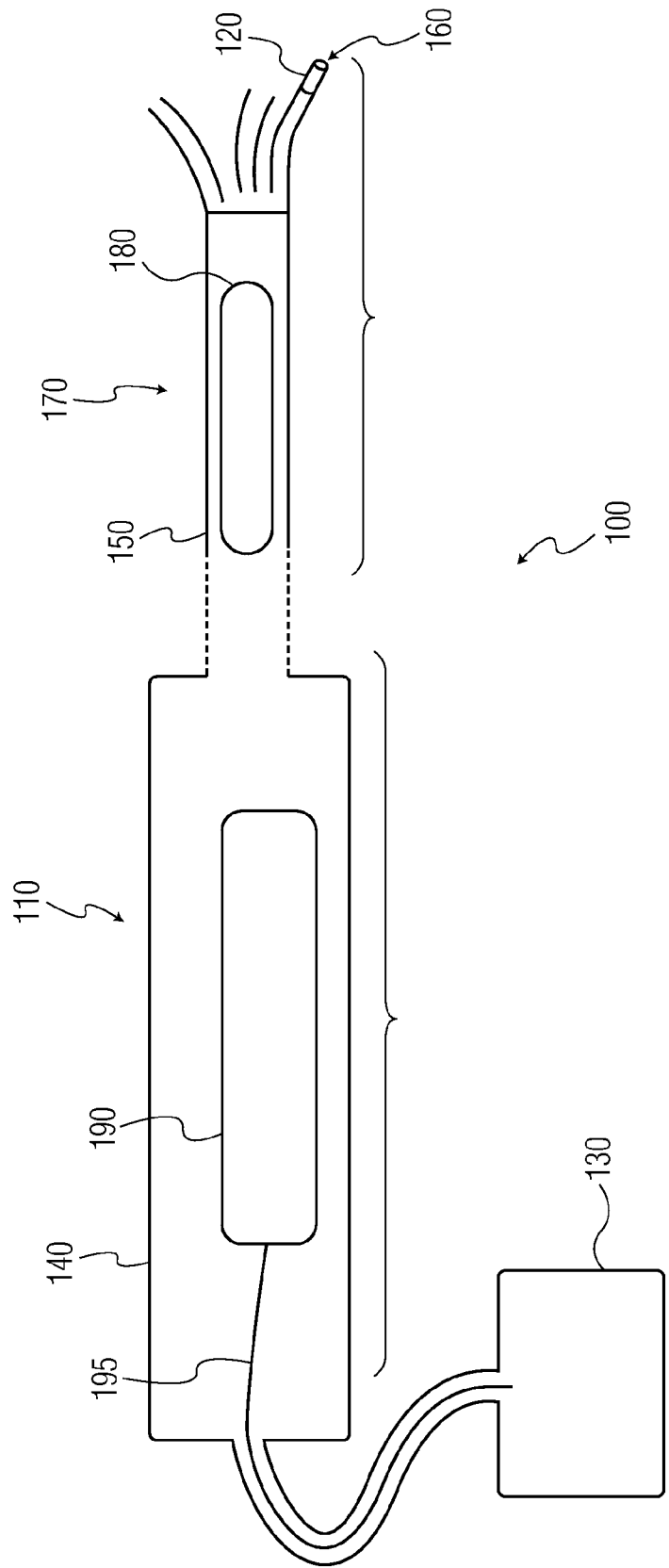
FIG. 1 is a diagram showing an exemplary first embodiment of a catheter.

FIG. 1 shows, by way of illustrative and non-limitative example, a catheter 100. The catheter 100 includes a catheter body 110 having a handle 140, and extending from the handle 140, an insertion end 170 for insertion into a patient. The insertion end 170 includes a sensor 120, a tube or sheath 150, and a local power-delivery/data-reception (PDDR) unit 180. The sensor 120 measures or senses a property of a patient (e.g., fluid flow, oxygen, pressure, location, etc) and is capable of sending a data signal reflective of the measured or sensed property. The tube or sheath 150 encloses an electrode 160 which is one of an array of electrodes. The sheath 150 is long enough to be inserted through the patient's vein and fed in to reach a bodily organ, such as the heart. Accordingly, FIG. 1 shows a broken line. The local power-delivery/data-reception (PDDR) unit 180 is configured for wirelessly communicating with the sensor 120 including wirelessly emitting a signal that powers the sensor 120 and wirelessly receiving data signals sent from the sensor 120. A remote PDDR unit 190 is located within the handle 140 for communicating with the local PDDR unit 180. A wire, such as a coaxial cable 195, is shown connecting the remote PDDR unit 190 to sensor control electronics 130, although the cable may be replaced by a wireless connection.

Notably, the insertion end 170, including the local PDDR unit 180, is advantageously disposed during operation entirely within the body of the patient. The rest of the catheter body 110 remains outside the patient. Close proximity between the local PDDR unit 180 and the sensor 120 results in efficient power transmission. Powering the sensor 120 activates the sensor 120 to conduct a reading and to send a data signal reflective of the reading to the local PDDR unit 180. The sensor 120 may have a memory device for storing the read data for use in forming the data signal. The technique of powering a passive transponder to enable the transponder to return a data signal is well-known in the art. Power and/or data signals may be frequency- or time-division multiplexed to avoid interfering with each other. For example, the data signals may be in the range of 2 KHz to 10 KHz, whereas the power signals may be in the range of 20 KHz to 200 KHz. The multiplexing, whether by time or frequency, may involve the power and data signals for multiple sensors distributed on the electrode array. It is possible for the sensor 120 to communicate with the local PDDR unit 180 using a magnetic field generated by a magnetic loop antenna to avoid interfering with the electrical potentials in the heart, and since the energy transmitted scales with frequency. The single magnetic loop antenna in the sensor 120 is operable to receive power signals and to transmit data signals. It is, however, within the intended scope of the invention to use separate antennas for power and data, or separate antennas for input and output of either data or power. In addition, the antenna(s) may be implemented as electro-static, rather than a magnetic loop.

The local PDDR unit 180 can likewise be powered by remote PDDR unit 190 since the proximity of units 180 and 190 makes energy transfer efficient. The remote PDDR unit 190 is powered by the sensor control electronics 130, via the cable 195 or wirelessly. Thus, the remote PDDR unit 190 relays power to the local PDDR unit 180, and receives data from the local PDDR unit 180. Frequency or time-division multiplexing may also be used to avoid interference in the communication between the local and remote PDDR units 180, 190 respectively. Preferably, the local PDDR unit 180 communicates by magnetic field with the remote PDDR unit 190. It is also preferable that the units 180, 190 each have a single antenna for power and data.

Figure 2:
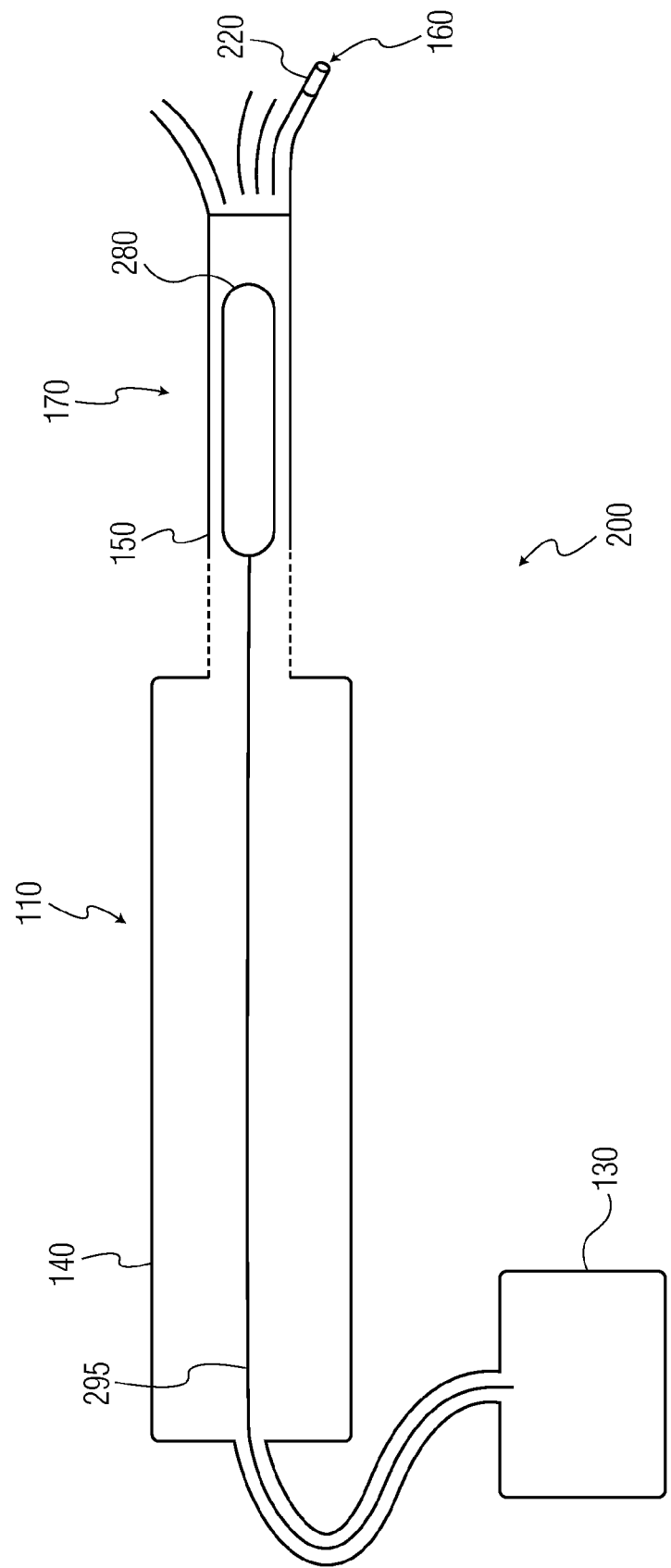
FIG. 2 is a diagram showing an exemplary second embodiment of a catheter.

FIG. 2 illustrates a second embodiment of the catheter 200. It differs from the first embodiment in that the remote PDDR unit is eliminated, and the cable 295 extends to the local PDDR unit 280. Advantageously, merely a single wire or cable 295 is needed to control an array of electrodes. The second embodiment of the catheter 200 also includes a sensor 220 which is embodied or incorporated in an integrated circuit (IC), discussed in more detail in FIG. 3B below.

It is possible for the sensor 220 to communicate with the local PDDR unit 180 using a magnetic field generated by a magnetic loop antenna to avoid interfering with the electrical potentials in the heart, and since the energy transmitted scales with frequency. The single magnetic loop antenna is operable to receive power signals and to transmit data signals. It is, however, within the intended scope of the invention to use separate antennas for power and data, or separate antennas for input and output of either data or power. In addition, the antenna(s) may be implemented as electro-static, rather than a magnetic loop. Thus, it is possible to incorporate a magnetic loop antenna or an electro-static antenna into an IC along with the sensor 220 and a corresponding magnetic loop antenna or an electro-static antenna into the local PDDR unit for wireless communication.

Figure 3A:
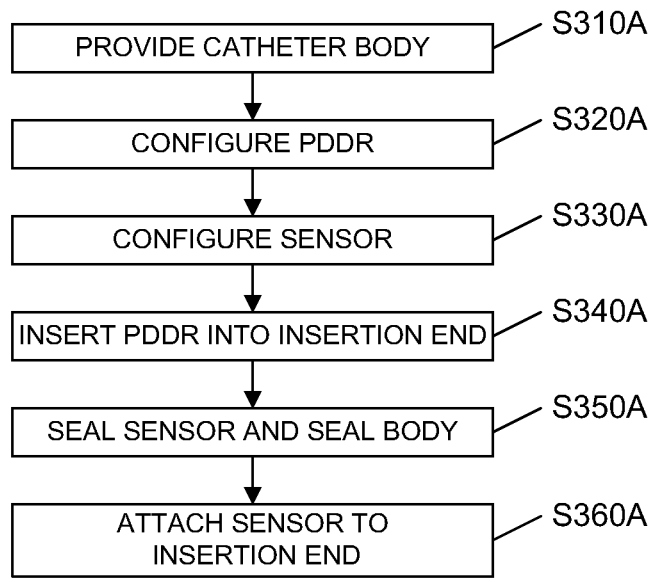
FIGS. 3A and 3B are flow charts of examples of processes for assembling a catheter.

FIG. 3A shows an exemplary method for making the catheter 100. A catheter body 110 having a handle 140 and an insertion end 170 is provided (S310A). A local power-delivery/data-reception (PDDR) unit 180, 280 to be incorporated at the insertion end 170 of the catheter body 110 is configured for wirelessly emitting a signal that powers a sensor 120 to be adjoined to the insertion end 170 and for wirelessly receiving a data signal from the sensor 120 (S320A). The sensor 120 to be adjoined to the insertion end 170 is configured for wirelessly receiving the emitted signal (for powering) and wirelessly sending, to the local PDDR unit, a data signal (S330A). The local PDDR unit is disposed within the insertion end 170 (S340A). The sensor 120 and the catheter body 110 are sealed, separately from each other (S350A). The sealed sensor is adjoined to the insertion end (S360A).

Figure 3B:
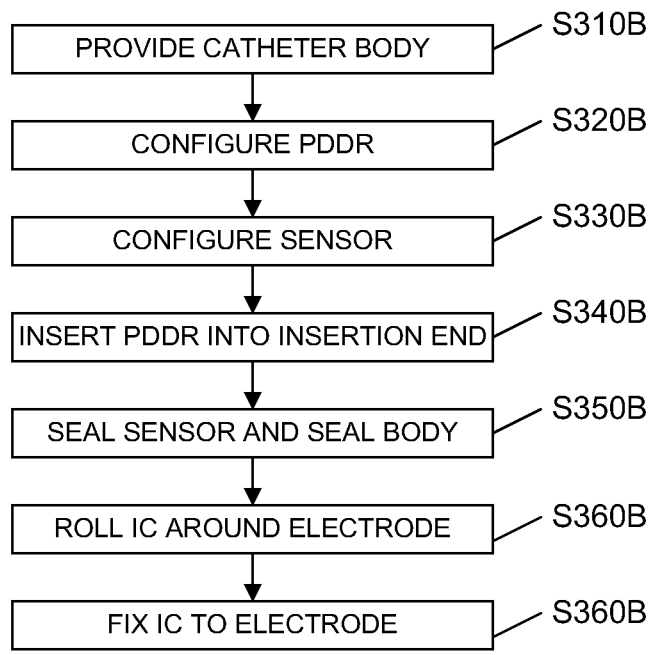

FIG. 3B shows an exemplary method for making the catheter 200, in which sensor 220 is embodied or incorporated in an integrated circuit (IC). A catheter body 110 having a handle 140 and an insertion end 170 is provided (S310B). A local PDDR unit 180, 280 to be incorporated at the insertion end 170 of the catheter body 110 is configured for wirelessly emitting a signal for powering the sensor 220 and receiving a data signal (step S320B). The sensor 220 to be adjoined is configured for wirelessly receiving the emitted signal (for powering) and wirelessly sending, to the local PDDR unit, a data signal (step S330B). The local PDDR unit 180, 280 is disposed within the insertion end 170 of the catheter body 110 (step S340B). The catheter body 110 and the sensor 220 are separately sealed and electrically insulated (step S350B). A polymer may be used for the sealing and insulating. The IC is then rolled around the end of the electrode 160 (step S360B). This requires that the IC be flexible. In the rolled position, the IC is fixed to the electrode 160, as by bonding with an adhesive, so that the IC remains fixed to the electrode during application of the catheter 200, i.e., during insertion and withdrawal of the catheter (step S370B).

Figure 4A:
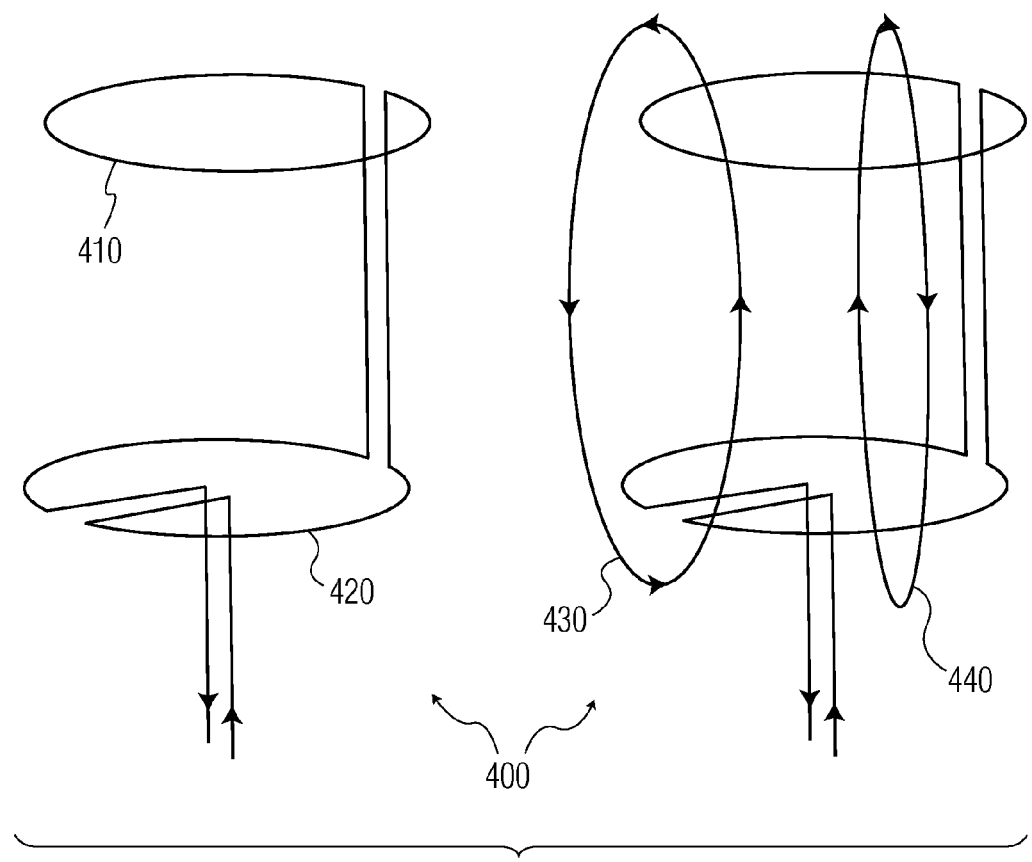
FIGS. 4A and 4B depict exemplary magnetic loop antennas.

FIG. 4A depicts one exemplary configuration for a magnetic loop antenna 400 utilizable in the local and remote PDDR units 180, 190. The antenna 400 includes two loops 410, 420 connected in series and residing in respective parallel planes. Paths 430, 440 of magnetic flux generated by the magnetic loop antenna 400 are also shown.

Figure 4B:
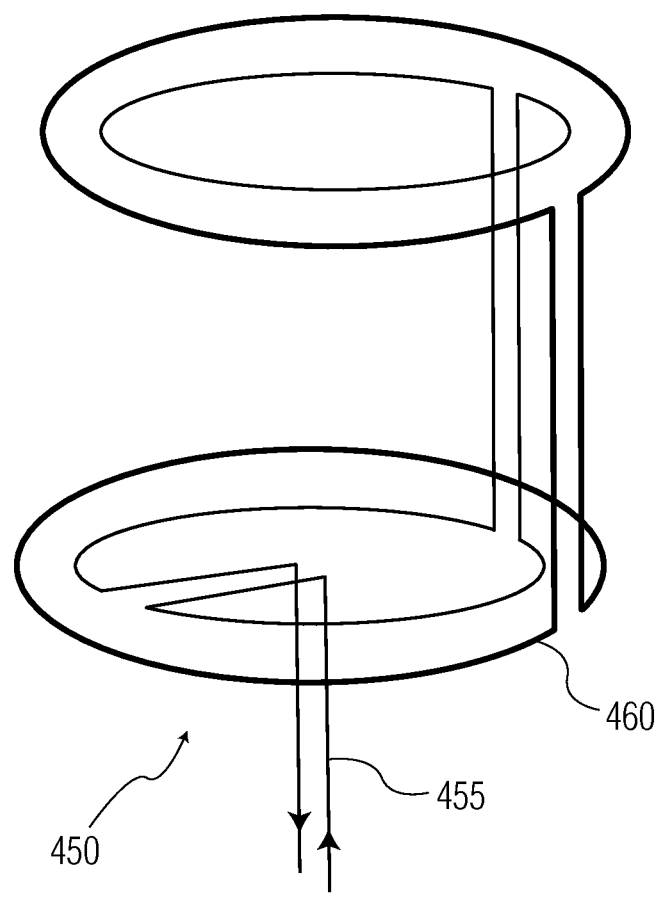

FIG. 4B shows a magnetic loop antenna 450 for a sensor 120 or sensor 220 embodied or incorporated in an IC, having an inner or primary coil 455 and an outer or secondary coil 460. The primary coil 455 is embedded in the secondary coil 460 so that the secondary coil encloses the flux generated during transmission. The two coils 455, 460 do not have an electrical connection between them. Instead they are coupled by mutual inductance. Physically the secondary coil 460 can be supported from the primary coil 455 by a dielectric such as a polymer.

Figure 5A:
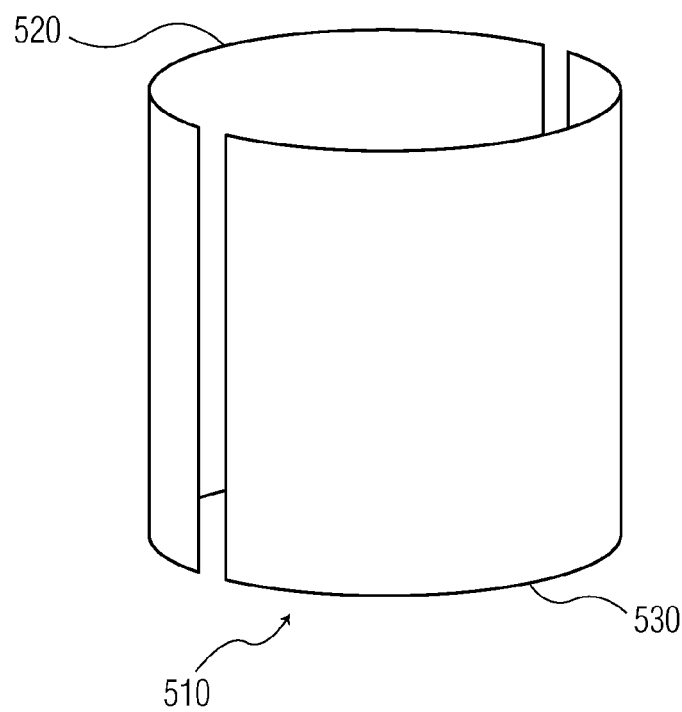
FIGS. 5A and 5B depict exemplary electro-static antennas.

FIG. 5A represents an alternative embodiment for an antenna wherein electro-static is used rather than magnetic loop. The antenna 510 for the units 180, 190 includes two hollow semi-cylinders 520, 530 of semi-circular cross-section.

Figure 5B:
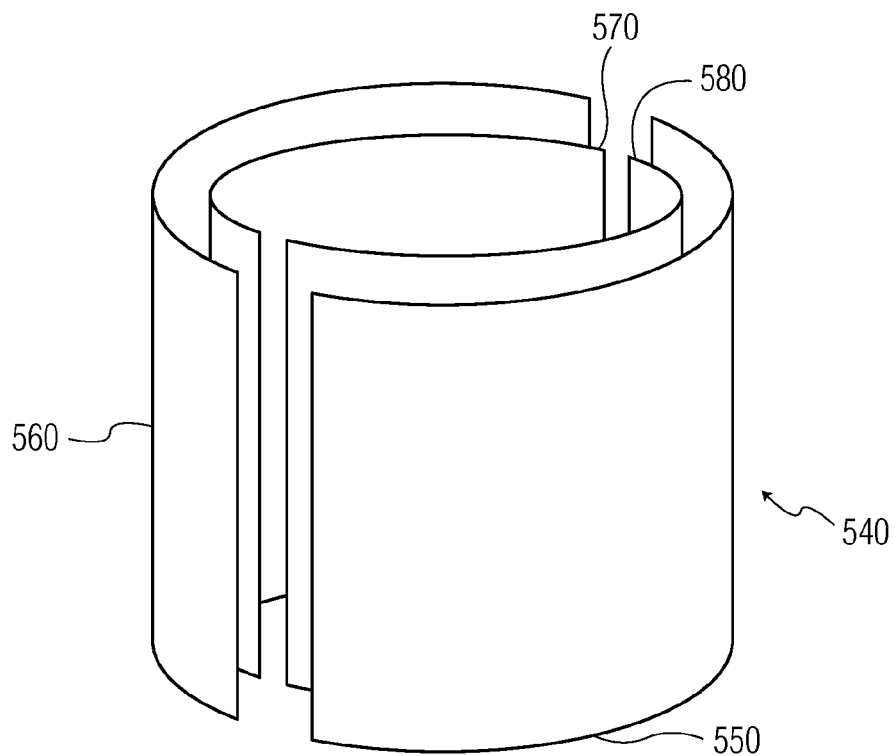

FIG. 5B shows an electro-static antenna 540 for a sensor 120 or sensor 220 embodied or incorporated in an IC, which includes an outer pair 550, 560 of semi-circular cylinders of semi-circular cross-section, with an inner pair 570, 580 being concentrically nested within the outer pair.

While the invention has been illustrated and described in detail in the drawings and foregoing description, such illustration and description are to be considered illustrative or exemplary and not restrictive; the invention is not limited to the disclosed embodiments.

For example, although the IC is disclosed as rolled axially around the electrode, the IC may be bent or flexed into other shapes as attached, or may be attached in a different location or orientation.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

What is claimed is:

1. A catheter, comprising:
   a sealed catheter body including a handle and an insertion end for inserting into a patient, and
   a sealed sensor adjoined to said insertion end, the sensor and catheter body being sealed from each other, and
   a local power-delivery/data-reception unit incorporated at the insertion end and configured for wirelessly emitting a radio signal that powers the sensor, said sensor being configured for wirelessly sending a data-containing radio signal to the local power-delivery/data-reception unit.

2. The catheter of claim 1, further comprising an integrated circuit incorporating the sensor such that the sealing seals the integrated circuit, the integrated circuit being flexible.

3. The catheter of claim 2, wherein said end includes an end of an electrode, the integrated circuit being rolled around the electrode end.

4. The catheter of claim 1, wherein said unit is electrically insulated from the sealed sensor.

5. The catheter of claim 1, further comprising one cable disposed longitudinally within the catheter body to extend between said unit and a controller for controlling the sensor, said cable being a coaxial cable.

6. The catheter of claim 1, further comprising a remote power-delivery/data-reception unit disposed within the handle and configured for wirelessly communicating with the local power-delivery/data-reception unit and a controller for controlling the sensor.

7. The catheter of claim 1, further comprising an integrated circuit incorporating the sensor and incorporating an electro-static antenna, said unit also incorporating an electro-static antenna, for communicating wirelessly with the electro-static antenna in the integrated circuit.

8. The catheter of claim 1, wherein the adjoining fixes so that the sealed sensor remains fixed to said end during said inserting and during withdrawal of the catheter from the patient.

9. A catheter, comprising:
a sealed catheter body including a handle and an insertion end for inserting into a patient, and
a sealed sensor adjoined to said insertion end, the sensor and catheter body being sealed from each other, and
a local power-delivery/data-reception unit incorporated at the insertion end and configured for wirelessly emitting an electromagnetic signal that powers the sensor, said sensor being configured for wirelessly sending an electromagnetic data signal to the local power-delivery/data-reception unit,
further comprising, for said returning by the sensor, a magnetic loop antenna having an inner coil and an outer coil, each coil having two loops in respective parallel planes, the inner loop being nested within the outer loop.

10. The catheter of claim 9, wherein the inner and outer coils are electrically isolated from each other and disposed to communicate energy with one another by mutual inductance.

11. The catheter of claim 9, wherein said unit comprises an antenna formed into a single coil, said coil having a single loop, said single loop residing in a single plane.

12. The catheter of claim 9, further comprising an integrated circuit incorporating the sensor such that the sealing seals the integrated circuit, the integrated circuit being flexible.

13. The catheter of claim 12, wherein said end includes an end of an electrode, the integrated circuit being rolled around the electrode end.

14. The catheter of claim 9, further comprising one cable disposed longitudinally within the catheter body to extend between said unit and a controller for controlling the sensor, said cable being a coaxial cable.

15. The catheter of claim 9, further comprising a remote power-delivery/data-reception unit disposed within the handle and configured for wirelessly communicating with the local power-delivery/data-reception unit and a controller for controlling the sensor.

16. A method for assembling a catheter, comprising:
providing a catheter body with a handle, and an insertion end for inserting into a patient;
configuring a local power-delivery/data-reception unit to be incorporated within said end for wirelessly emitting a radio signal that powers a sensor to be adjoined to said end;
configuring the sensor for wirelessly sending, to the local power-delivery/data reception unit, a data-containing radio signal;
disposing the local power-delivery/data reception unit within said end;
sealing the sensor and the catheter body so that they are sealed from each other; and
adjoining the sealed sensor to said end.

17. The method of claim 16, wherein said configuring of the sensor comprises embodying the sensor in an integrated circuit such that the sealing seals the integrated circuit, said adjoining comprising flexing the integrated circuit.

18. The method of claim 17, wherein said providing provides, as part of said end, an end of an electrode, said flexing comprising rolling the integrated circuit around the electrode end.

19. The method of claim 16, comprising electrically isolating said unit from the sensor.

20. The method of claim 16, further comprising disposing a remote power-delivery/data-reception unit within the handle for wirelessly communicating with the local power-delivery/data-reception unit.

21. The method of claim 16, wherein said adjoining comprises fixing so that the sealed sensor remains fixed to said end during said inserting and during withdrawal of the catheter from the patient.

22. A method for assembling a catheter, comprising:
providing a catheter body with a handle, and an insertion end for inserting into a patient;
configuring a local power-delivery/data-reception unit to be incorporated within said end for wirelessly emitting an electromagnetic signal that powers a sensor to be adjoined to said end;
configuring the sensor for wirelessly sending, to the local power-delivery/data reception unit, an electromagnetic data signal;
disposing the local power-delivery/data reception unit within said end;
sealing the sensor and the catheter body so that they are sealed from each other; and
adjoining the sealed sensor to said end,
wherein said configuring of the sensor comprises providing a magnetic loop antenna having an inner coil and an outer coil, each coil having two loops in respective parallel planes, the inner loop being nested within the outer loop, wherein said providing of the magnetic loop antenna comprises configuring the inner and outer coils to be electrically isolated from each other and disposed to communicate energy with one another by mutual inductance.

* * * * *